United States Patent
Podzus

(10) Patent No.: US 7,135,299 B2
(45) Date of Patent: Nov. 14, 2006

(54) CATALASE-INACTIVATING COMPOUNDS AND THE USE THEREOF

(76) Inventor: Bernd Fritz Podzus, Dachsen (CH)

( * ) Notice: Subject to any disclaimer, the term of this patent is extended or adjusted under 35 U.S.C. 154(b) by 28 days.

(21) Appl. No.: 10/482,792

(22) PCT Filed: May 17, 2002

(86) PCT No.: PCT/CH02/00270

§ 371 (c)(1),
(2), (4) Date: Jan. 2, 2004

(87) PCT Pub. No.: WO03/004462

PCT Pub. Date: Jan. 16, 2003

(65) Prior Publication Data

US 2004/0191838 A1 Sep. 30, 2004

(30) Foreign Application Priority Data

Jul. 2, 2001 (CH) .................................... 1205/01

(51) Int. Cl.
*G01N 33/567* (2006.01)
*G01N 33/53* (2006.01)
*C07C 309/00* (2006.01)

(52) U.S. Cl. ........................... 435/7.2; 562/30; 435/27; 435/183

(58) Field of Classification Search ................. 435/7.2, 435/27, 183; 562/30
See application file for complete search history.

(56) References Cited

U.S. PATENT DOCUMENTS 5,610,025 A 3/1997 White et al.

FOREIGN PATENT DOCUMENTS

EP 0184260 11/1985

OTHER PUBLICATIONS

Lobo et al., The S->O Acyl Shift in S-Acylthiol S-Oxides Mixed Sulphonic Acid Carboxylic Acid Anhydrides From Thiolesters, Tetrahedron Letters No. 25, pp. 2171-2174, 1978.*
WO 93/15218 A—PCT International Application PCT/US93/00771 filed Jan. 28, 1993.

* cited by examiner

*Primary Examiner*—James O. Wilson
*Assistant Examiner*—Chukwuma Nwaonicha
(74) *Attorney, Agent, or Firm*—Galgano & Burke, LLP

(57) ABSTRACT

The invention relates to the sulfonyl esters of the general formula $R_1$—COO—$SO_2$—Z—$R_2$, wherein Z, $R_1$ and $R_2$ are defined as in claim 1. The invention further relates to the use of one of the inventive compounds for modifying the kinetics of the enzymatic effect of catalase. A method for measuring a concentration in living and/or active microorganisms in a liquid sample (3) by means of the development of oxygen from hydrogen peroxide is also based on the above-mentioned modification. An inventive compound is admixed in a container (1) to the sample, said compound inactivates the enzymatic effect of endogenous catalase without substanially inactivating the enzymatic effect of the intracellular catalase of microorganisms. Hydrogen peroxide is added and immediately afterwards the pressure present in the sample container is briefly equalized with the atmosphere, the container is closed in a gas-tight manner (2) during a predetermined reaction time and the pressure in the container is measured (9, 10, 11). The pressure measured and the data regarding the microorganisms and the sample dilution are used to calculate (22) the concentration of living and/or active microorganism in the sample and the concentration is optionally displayed (24). The invention further relates to a device for carrying out the inventive method.

23 Claims, 2 Drawing Sheets

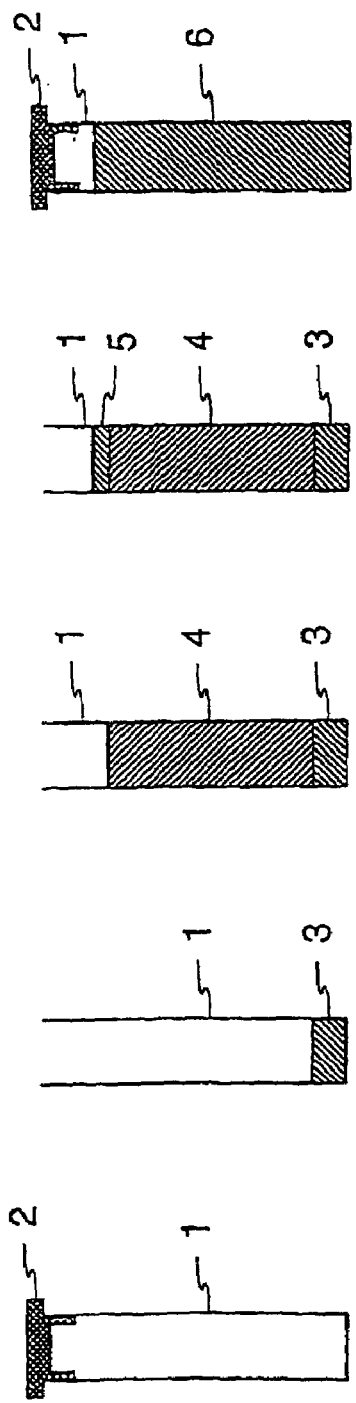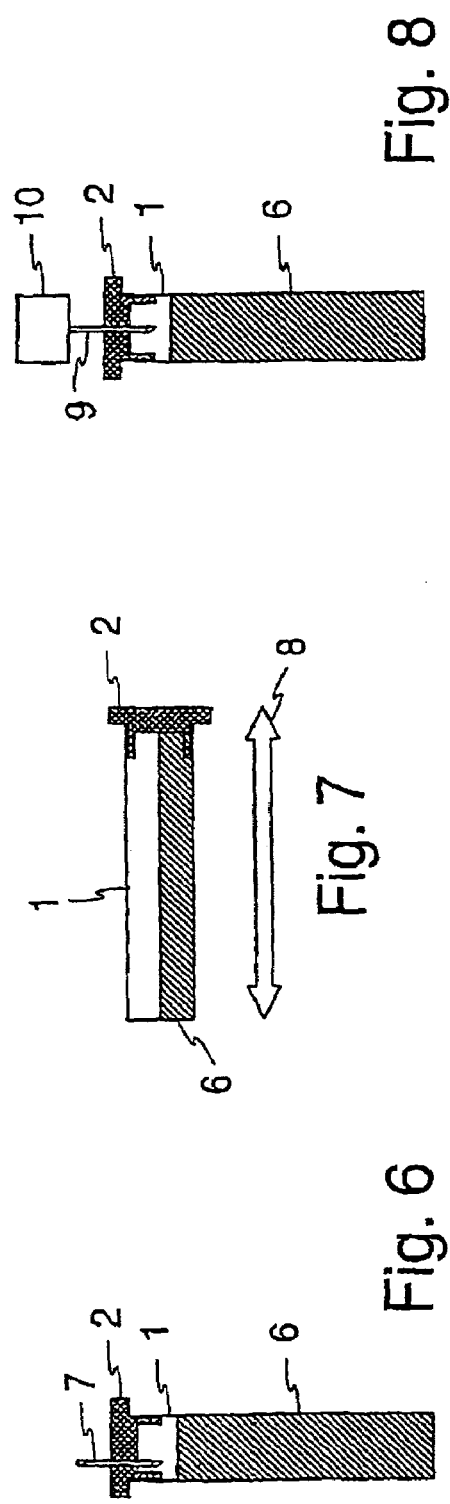

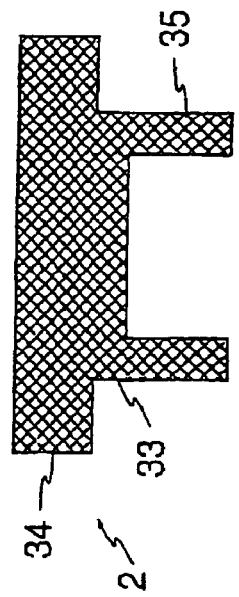
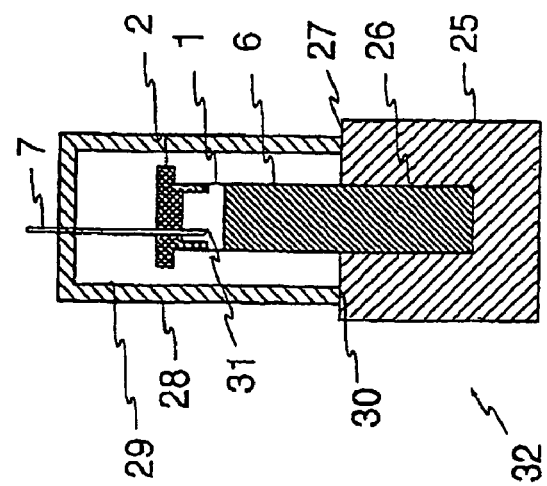
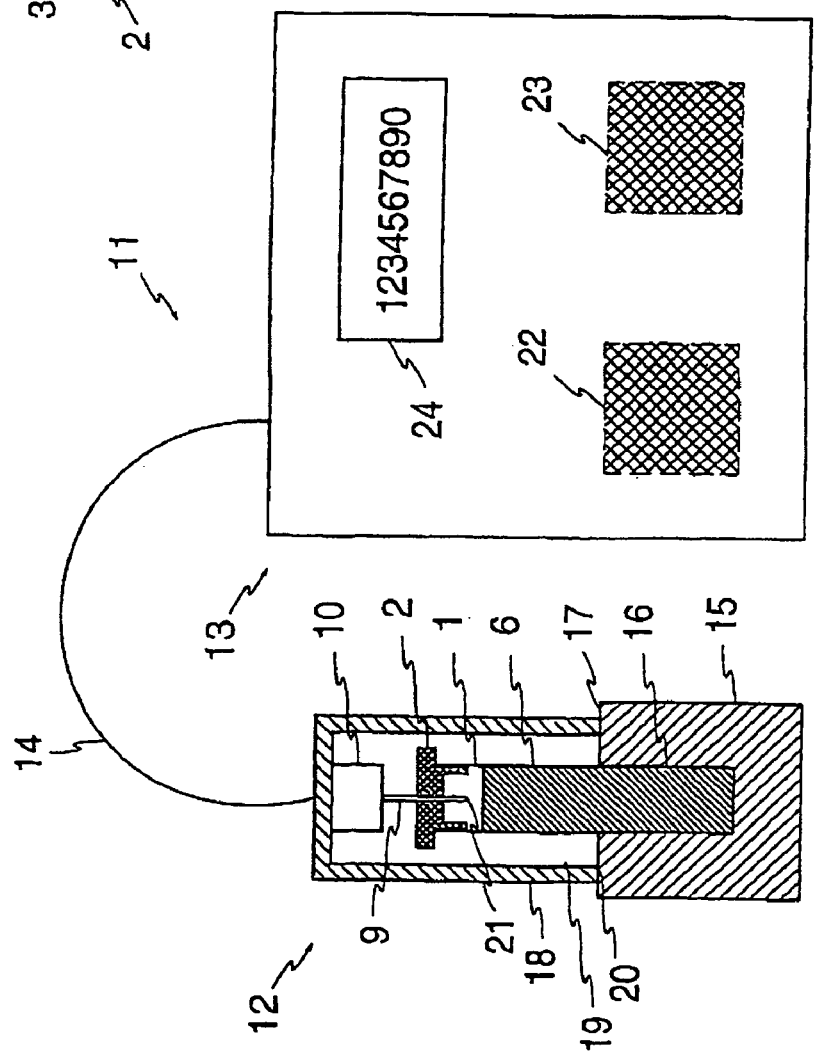

CATALASE-INACTIVATING COMPOUNDS AND THE USE THEREOF

RELATED APPLICATION

This Application is a 371 of PCT/CH02/00270 May 17, 2002 published as WO 03/004462A1 on Jan. 16, 2003.

TECHNICAL FIELD

The invention relates to sulfonyl esters of the general formula $R_1$—COO—$SO_2$—Z—$R_2$ in which Z, $R_1$ and $R_2$ have the meanings defined in claim 1, to a use of these compounds for modifying the kinetics of the enzymatic action of catalase, to a method for measuring a concentration of live and/or active microorganisms such as bacteria and/or fungi, especially molds and/or yeasts, in a liquid sample by means of the evolution of oxygen from hydrogen peroxide, and to an apparatus for carrying out this method.

PRIOR ART

Determination of the microbial contamination of foodstuffs, cooling lubricants and the like, or else the investigation of the efficacy of a biocide or disinfectant, currently takes place mainly by microbiological methods which make use of a growth of the microorganisms to be determined and are therefore slow and unsuitable for continuous monitoring of the microbial contamination on site.

The principal causes of microbial contamination are in the case of foodstuffs mainly aerobic microorganisms (such as bacteria and/or fungi, especially molds and/or yeasts) and in the case of aqueous cooling lubricant emulsions also microorganisms which are facultative anaerobes. All microorganisms which have a respiratory system based on cytochrome electron transport to generate energy (and these are almost all microorganisms occurring in foodstuffs and cooling lubricant emulsions) have a particular enzyme called catalase which chemically is a tetrameric iron-protein ($M_r$=245000) with 4 heme mol in the form of ferriprotoporphyrin IX with iron(III). Catalase extremely rapidly cleaves hydrogen peroxide into water and oxygen, and the oxygen evolution is directly proportional to the enzyme concentration. This is the basis for a known method for determining the microbial contamination, which is faster than methods dependent on growth of microorganisms—compare in this connection H. K. Frank & U. Hertkorn-Obst, Chem. Mikrobiol. Technol. Lebensm. 6, 143–149 (1980) and/or R. G. Kroll, E. R. Frears & A. Bayliss, J. Appl. Bacteriol. 66, 209–217 (1989). Measurement of the oxygen evolution is possible in various known ways, inter alia by manometry—compare in this connection G. J. Wang and D. Y. C. Fung, J. of Food Safety 8, 46–47 (1986) and EP-476850. It is known to be advantageous to put the microorganisms to be determined into an aqueous sample and to add hydrogen peroxide in an amount resulting in a concentration of about 1% by volume, the optimal pH for the measurement for most microorganisms to be determined being in the neutral region at 7.

Another requirement for determining the microbial contamination of an investigated material or a sample thereof is to detect only the live microorganisms, i.e. only the enzymatic action of the active intracellular catalase of these live microorganisms is important and requires measurement. However, measurement errors result from the enzymatic action of active endogenous catalase from a wide variety of sources present in the sample. Thus, various difficulties are reported both by H. K. Frank & U. Hertkorn-Obst and by R. G. Kroll, E. R. Frears & A. Bayliss. A special effort must be made to distinguish between live and dead yeast cells (brewer's yeast). Foodstuffs contain non-microbial endogenous catalase which is introduced into the sample by plant constituents (lettuce, onions), juice (apple juice, lemon juice) and animal tissue (erythrocytes in meat and milk), and markedly falsifies the measurement through its enzymatic action unless the action of this non-microbial endogenous catalase has been previously eliminated for example by heat treatment (pasteurization, preservation). Drinking water and superfluous water also contain interfering plant residues and suspended matter of a wide variety of types, which catalyze oxygen evolution as soon as hydrogen peroxide is introduced into the sample, unless these interfering substances are eliminated by filtration.

The abovementioned difficulties make the currently available, relatively fast methods for determining the microbial contamination of foodstuffs, cooling lubricants and the like, as well as for investigating the activity of a biocide or disinfectant, unreliable.

EP-184260 discloses a method with which the total catalase content, but not the concentration of live and/or active microorganisms is detected. In this method, both the bacterial and the non-bacterial, i.e. endogenous, catalase is detected, leading to considerable differences. Thus, owing to the imperfect relationship between the number of colony-forming units (CFU) and the catalase levels under the influence of biomass, an assessment of the microbial contamination or measurement of the concentration of live and/or active microorganisms is not possible in every case.

U.S. Pat. No. 5,610,025 and/or WO-93/15218 discloses a method with which hydrogen peroxide-decomposing enzymes are detected in the presence of catalase. Addition of the hydrogen peroxide is preceded by inhibition of catalase by addition of a hydroxylamine salt. This teaching does not lead to a measurement of the concentration of live and/or active microorganisms.

It is accordingly an object of the invention to provide a method for measuring a concentration of live and/or active microorganisms whose measured results are reliable and, in particular, are not falsified by endogenous catalase.

It is accordingly also an object of the invention to indicate and provide chemical compounds which bring about a modification of the kinetics of the enzymatic action of catalase, in particular a preferably irreversible inactivation of the enzymatic action of catalase, in particular of active endogenous catalase, in particular without noticeable inactivation of the enzymatic action of active intracellular catalase.

It is likewise an object of the invention to provide a method of the aforementioned type, whose measured results can be obtained and interpreted rapidly, and an apparatus suitable therefor.

DESCRIPTION OF THE INVENTION

To achieve these and further objects which are evident from the following description of the invention, novel chemical compounds of the invention are indicated and their uses according to the invention are defined in the corresponding product claims and use claims.

A method according to the invention and preferred further developments thereof are likewise defined in the corresponding method claims, and a preferred apparatus according to the invention for carrying out the method according to the invention and preferred further developments thereof are defined in the corresponding apparatus claims.

Owing to the simplicity of the method according to the invention, especially in connection with the apparatus according to the invention for carrying it out, the invention makes it possible to carry out the method easily, rapidly and cost-effectively, with direct indication of a concentration of live and/or active microorganisms being made possible.

Since both the reaction time and the measurement time are short in the method according to the invention, there is the possibility for example of subjecting a foodstuff immediately before marketing or shortly before consumption to a check so that batches with a microbial contamination which is too high can be withheld in good time.

In particular, the measured results of the method according to the invention can be obtained within a shorter time than, for example, half an hour and therefore currently (virtually in real time), making use thereof possible on site for controlling and/or monitoring a method, where the active intracellular catalase is that of live microorganisms such as bacteria and/or fungi, especially molds and/or yeasts.

In addition, the chemical compounds indicated and provided by the invention bring about a modification of the kinetics of the enzymatic action of catalase, which makes it possible to use them for killing microorganisms.

BRIEF DESCRIPTION OF THE DRAWINGS

Exemplary embodiments of the invention are described in detail below by means of the drawings. These show:

FIG. 1 to 8 consecutive steps in a method according to the invention by means of diagrammatic depictions of articles and liquids used therefor;

FIG. 9 a diagrammatically depicted pressure gage of an apparatus for carrying out the method according to the invention having a pressure probe part and a pressure evaluation part each depicted diagrammatically;

FIG. 10 a diagrammatically depicted ventilation implement of an apparatus for carrying out the method according to the invention; and FIG. 11 a diagrammatically depicted stopper for use with an apparatus for carrying out the method according to the invention.

WAYS OF CARRYING OUT THE INVENTION

It has been found within the scope of the invention that particular chemical compounds are able to modify the kinetics of the enzymatic action of catalase. This modification may be different with active endogenous catalase or active intracellular catalase. Depending on the chemical compound used and on the type of catalase modified thereby (endogenous or intracellular, in the latter case present in cells of different microorganisms), this modification may effect irreversible inactivation of all the catalase, and/or an irreversible inactivation of active endogenous catalase without noticeable inactivation of the enzymatic action of active intracellular catalase can be achieved. A variety of applications derive therefrom, among which the measurement of a concentration of live and/or active microorganisms and/or the killing of microorganisms are of particular interest.

Microorganisms suitable in this connection may be bacteria and/or fungi, especially molds and/or yeasts.

Chemical compounds suitable in this connection are sulfonyl esters of the general formula $$R_1-COO-SO_2-Z-R_2$$

in which

Z is phenylene or is absent, $R_1$ is connected via a primary or secondary carbon atom to the carbon atom of the acid radical —COO— and is straight-chain or branched alkyl having 2 to 21000 carbon atoms, straight-chain or branched alkenyl having 2 to 21000 carbon atoms, or straight-chain or branched alkynyl having 2 to 21000 carbon atoms, and $R_2$ is connected via a secondary or tertiary carbon atom to the phenylene radical in the position ortho, meta or para to the $SO_2$ radical when Z is present, or to the $SO_2$ radical when Z is absent, and is straight-chain or branched alkyl having 3 to 100 carbon atoms, straight-chain or branched alkenyl having 3 to 100 carbon atoms, straight-chain or branched alkynyl having 3 to 100 carbon atoms, straight-chain or branched alkoxy having 3 to 100 carbon atoms, straight-chain or branched hydroxyalkyl having 3 to 100 carbon atoms, where the hydroxyl radical is connected via a primary or secondary carbon atom to the alkyl radical, or polyoxaalkyl having 3 to 100 carbon atoms.

Preferred compounds among these are, inter alia:

$$CH_2=CH-COO-SO_2-\langle\bigcirc\rangle-C_{12}H_{25},$$

$$CH_2=CH-COO-SO_2-CH\underset{(CH_2)_m-CH_3}{\overset{(CH_2)_n-CH_3}{<}},$$

in which n and m are natural numbers and 3<(n+m)<60, $$CH_2=CH-COO-SO_2-CH_2-CH=CH-C_{13}H_{27},$$

$$CH_2=CH-COO-SO_2-O-C_{12}H_{25},$$

$$CH_2=CH-COO-SO_2-CH_2-CH_2-\underset{OH}{\overset{|}{CH}}-C_{13}H_{27},$$

and $$CH_2=CH-COO-SO_2-O-CH_2-CH_2-O-CH_2-CH_2-O-C_{12}H_{25}.$$

Preparation and Investigation of the Compound $$CH_2=CH-COO-SO_2-\langle\bigcirc\rangle-C_{12}H_{25}$$

460 ml of distilled water are put into a 1000 ml Erlenmeyer flask and then 94 g of sodium dodecylbenzenesulfonate are added. The mixture is stirred with a magnetic stirrer at about 50° C. until dissolution is complete, and then the solution is left to stand for about 15 minutes to cool. Then 2.4 ml of anhydrous acrylic acid are slowly added while stirring, and the solution is stirred further until it reaches room temperature. After this solution has been left to stand in the dark at room temperature for at least 24 hours, 79.5 ml of distilled water are put into a 250 ml Erlenmeyer flask, and then 0.5 ml of a 0.066 M phosphate buffer solution (pH 7.00) is added while stirring. Subsequently, 1 g of the solution mixture obtained the previous day is added while stirring. The resulting solution of the title compound has a pH of about 4.6.

The following reagents are provided:
catalase from ox liver (as active endogenous catalase)
catalase from *Aspergillus niger* (as active intracellular catalase)
catalase from microorganisms[*] (as active intracellular catalase)
antifoam (RD® from Dow Corning)
hydrogen peroxide (Perhydrol® 30% from Merck)

[*]various bacteria and/or fungi

Each sample contains in each case 35 units of catalase from ox liver or from *Aspergillus niger* or from microorganisms per ml of distilled water. The 1 ml sample is put in a 15 ml tube (Vacutainer® 16×125 mm from Becton Dickinson), and in each case 7 ml of the aforementioned solution of the title compound are added and mixed therewith (Vortex® Genie 2 mixer from Merck). Then 1 drop of said antifoam is added and mixing is repeated. Thereafter 0.23 g of said hydrogen peroxide is added, and the tube is immediately made gas-tight with a stopper made of chemical-resistant elastic plastic (Viton® from Du Pont de Nemours), briefly (for a few seconds) ventilated with the aid of a hollow needle (Ø1 mm hypodermic needle) piercing the stopper and, immediately thereafter, closed gas-tight again by withdrawing the hollow needle from the stopper. The tube which has been closed gas-tight is left to stand at room temperature for 15 minutes. The tube which has been tilted to the horizontal is then shaken back and forth 10 times in order to ensure that the cell membranes burst open. The pressure in the tube is then measured (cf. the description hereinafter of the preferred pressure gage).

It is found that the pressure in the tube does not increase. It follows from this that the title compound inactivates both active endogenous catalase and active intracellular catalase. It also follows from this that the title compound can be used to kill microorganisms, because these microorganisms whose intracellular catalase is inactivated die because of the absence of the action of this catalase.

Preparation and Investigation of the Compound

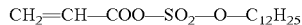

200 ml of distilled water are put into a 500 ml Erlenmeyer flask, and then 25 g of sodium lauryl sulfate are added. The mixture is stirred with a magnetic stirrer at about 70° C. until dissolution is complete. Then, while maintaining the temperature, 1.07 g of polyacrylic acid ($M_r$=500000 to 1000000) are slowly added while stirring, and the solution is stirred for a further 45 minutes. Subsequently, 5 ml of a 0.25 M solution of disodium hydrogen phosphate dihydrate in distilled water are added, and then 2 ml portions of the solution are metered in every 15 minutes until a total of 12 ml of the solution has been used. The resulting solution mixture is initially stirred further while maintaining the temperature for 60 minutes and then cooled to room temperature. The solution mixture obtained in this way has a pH of about 5.9. Then 42 ml of distilled water are put in a 250 ml Erlenmeyer flask, and thereafter 5 ml of a 0.066 M phosphate buffer solution (pH 7.00) are added while stirring. Subsequently, 3 g of the solution mixture obtained previously are added while stirring. The resulting solution of the title compound has a pH of about 6.4

The same reagents as previously described in the preceding text are provided, and the catalase is exposed to the action of the title compound, and the catalase activity resulting thereafter is investigated by means of the oxygen evolution (increasing pressure), in the same way as in the preceding text.

If only active endogenous catalase is present in the sample, it is found that the pressure in the tube does not increase. If, however, active intracellular catalase from microorganisms such as bacteria and/or fungi, especially molds and/or yeasts, is also present in the sample, it is found that the pressure in the tube increases. It follows from this that the title compound inactivates active endogenous catalase but does not noticeably inactivate active intracellular catalase.

Uses of the Compounds of the Invention

The preceding examples of the preparation and investigation of chemical compounds of the invention show that the latter bring about a modification of the kinetics of the enzymatic action of catalase. It has emerged that a reversible or irreversible inactivation of the enzymatic action of catalase results depending on the compound of the invention used and depending on the microorganisms treated therewith, it being possible by suitable choice of the chemical compounds of the invention to inactivate the enzymatic action either only of active endogenous catalase or both of the latter and of active intracellular catalase, in particular from live microorganisms such as bacteria and/or fungi, in particular molds and/or yeasts.

Chemical compounds of the invention which irreversibly inactive the enzymatic action of active intracellular catalase of live microorganisms such as bacteria and/or fungi, in particular molds and/or yeasts, bring about the death of these microorganisms.

The procedure for using the chemical compounds of the invention for measuring a concentration of live and/or active microorganisms such as bacteria and/or fungi, in particular molds or yeasts, is described below.

Method for Measuring a Concentration of Live and/or Active Microorganisms in a Sample Liquid The method according to the invention for measuring a concentration of live and/or active microorganisms in a sample liquid is described below by means of FIGS. 1 to 8. It is based on the determination of the evolution of oxygen from hydrogen peroxide which is added to the sample liquid, which has been diluted and/or buffered where appropriate, and is broken down rapidly to oxygen and water by catalase present in the sample liquid.

FIG. 1 shows a provided essentially cylindrical container in one embodiment as test tube 1 which is, for example, a 15 ml Vacutainer® 16×125 mm tube from Becton Dickinson and can be closed gas-tight with a stopper 2 which is made of chemical-resistant elastic plastic, for example of Viton® from Du Pont de Nemours, and can be placed thereon. For illustration, the stopper 2 is depicted placed on the test tube 1 in FIG. 1.

FIG. 2 illustrates introduction of 1 ml of the sample liquid 3 to be investigated into the test tube 1. It is not depicted here that the sample liquid 3 has been obtained where appropriate from an original sample by dilution and/or buffering (preferably to a pH between 6 and 7).

FIG. 3 illustrates admixture of 7 ml of a reagent liquid 4 which is an approximately 0.05 M aqueous solution of the active substance of the invention, i.e. of a chemical compound of the invention or of a mixture of chemical compounds of the invention, to the sample liquid 3. The active substance of the invention is chosen in this case, with a view to the desired measurement of a concentration of live and/or active microorganisms, so that it inactivates the enzymatic action of any endogenous catalase present in the sample liquid, but does not noticeably inactivate the enzymatic action of intracellular catalase of the microorganisms to be measured.

FIG. 4 illustrates admixture, preferably by metered dropwise addition, of about 0.2 ml (about 0.23 g) of a 30% by weight aqueous hydrogen peroxide solution 5 to the amounts of liquids 3 and 4 illustrated in FIG. 3, after which a concentration of about 1% by volume of hydrogen peroxide is set up in the mixture 6 (illustrated in FIG. 5) resulting after mixing has taken place. It is helpful where appropriate to add one or a few drops of antifoam before addition of the hydrogen peroxide solution.

FIG. 5 illustrates the stopper 2 being placed on the test tube 1 immediately after the addition, illustrated in FIG. 4, of hydrogen peroxide solution 5, in order to close the mixture 6 gas-tight therein.

FIG. 6 illustrates piercing of the stopper 2, immediately after the gas-tight closure of the test tube 1 therewith illustrated in FIG. 5, with a hollow needle 7 which is, for example, a Ø1 mm hypodermic needle, after which the gas pressure prevailing in the test tube 1 equals atmospheric pressure. After a few, preferably 1 to 2, seconds, the hollow needle 7 is withdrawn from the stopper 2, after which the latter closes gas-tight, owing to its elasticity and because it is radially compressed in the region of the test tube 1, a (not depicted) pierced channel left behind by the withdrawan hollow needle 7.

FIG. 7 illustrates the mixture 6 then remaining gas-tight in the closed test tube 1 for a predetermined reaction time, which is counted from the withdrawal of the hollow needle 7 from the stopper 2, preferably for 15 minutes and, during this, being shaken in the test tube 1 which has been tilted horizontal, preferably by vigorous shaking back and forth 10 times, which is symbolized by the double-headed arrow 8. During this reaction time, oxygen is evolved from the hydrogen peroxide present in the mixture 6.

FIG. 8 illustrates measurement of the pressure prevailing in the test tube 1 at the end of the predetermined reaction time by piercing the stopper 2 with a hollow needle 9, which is likewise, for example, a Ø1 mm hypodermic needle, this hollow needle 9 being connected to a diagrammatically depicted pressure sensor 10. This pressure sensor 10 is in turn part of a pressure gage 11 which is described in detail hereinafter in connection with FIG. 9.

It is evident from comparison of FIGS. 6 and 8 that the stopper 2 is pierced by hollow needle 7 (for pressure equalization) and by hollow needle 9 (for pressure measurement) at different places in order to avoid an escape of gas from test tube 1 when hollow needle 9 is inserted into the (not depicted) pierced channel left behind in stopper 2 by withdrawn hollow needle 7 (and measurement errors resulting therefrom).

When the method according to the invention is carried out, it is normally known whether and in what ratio the investigated material or the sample thereof has been diluted in order to afford the sample liquid 3. It is also normally known, from experience, what types of microorganisms prevail in the investigated material, so that the efficiency or the activity of the catalase occurring in the investigated material is normally also known. It is possible with the aid of this information and after a blank and, with known concentrations of microorganisms of the same type, a characteristic curve of the pressure gage 11 has been measured, to calculate the concentration of live and/or active microorganisms in the sample from the measured pressure. It is easy and requires no detailed description here to provide a microprocessor 22 and data memory 23 in the pressure gage 11 (cf. concerning this the description hereinafter in connection with FIG. 9) in order to store said data therein and process it so that the concentration of live and/or active microorganisms in the sample is automatically calculated and preferably displayed directly as numerical value.

Apparatus for Measuring a Concentration of Live and/or Active Microorganisms in a Sample Liquid FIG. 9 illustrates a pressure gage, designated overall by 11, of an apparatus for carrying out the method of the invention. The pressure gage 11 includes a diagrammatically depicted pressure probe part, designated overall by 12, and a diagrammatically depicted pressure evaluation part, designated overall by 13, which are connected together by electric leads of a shielded multicore electric cable 14.

The pressure probe part 12 includes a base 15 in the form of a cylindrical blind socket whose bore 16 is disposed with the axis vertically during use. The test tube 1 fits with little play in this bore 16, and it can be introduced axially therein to about one half of its length. An annular rim of the base 15 at the end of the bore 16 forms a stop face 17 which is coordinated with the test tube 1, which has been completely inserted into the bore 16, and is in a predetermined position in relation to this tube, irrespective of whether and how far a stopper 2 has been pushed into the test tube 1 in order to close the latter. The pressure probe part 12 additionally includes the previously mentioned hollow needle 9 and the previously mentioned pressure sensor 10, and a cylindrical blind positioning socket 18 whose bore 19 is disposed with the axis vertically during use. The hollow needles 9 are firmly disposed, coaxially to the bore 19, on the pressure sensor 10, and the latter is firmly disposed on the positioning socket 18. An annular rim of the positioning socket 18 at the end of the bore 19 forms a stop face 20 in fixed position and coordination with the positioning socket 18 and consequently, via the pressure sensor 10 and the hollow needle 9, with the tip 21 thereof. The axial length of the positioning socket 18 is such that, on use of the pressure probe part 12, the stopper 2 is pierced by the hollow needle 9 to such an extent, and the latter can be introduced into the interior of the test tube 1 only to such an extent, that its tip 21 remains above the mixture 6 present in the test tube 1, in a headspace located there. Finally, as is evident from FIG. 9, the pressure probe part 12, the test tube 1 and the stop faces 17 and 20 coordinated therewith have dimensions and are positioned relative to one another in such a way that, when the stopper 2 is pierced by the hollow needle 9, only the latter comes into contact with the stopper 2, so that the latter is stressed only slightly and mainly only radially, and consequently is not pushed into the interior of the test tube 1, which would cause a volume change and measurement errors resulting therefrom, which are thus avoided.

The pressure evaluation part 13 includes a microprocessor 22 and data memory 23, which receive data from the pressure sensor 10 in the pressure probe part 12 via cable 14. In addition, at least some of the data memories 23 (for example as EPROM, flash memory or other exchangeable and employable memories), and thus also the microprocessor 22, are programmable. It is thus possible to store in the pressure evaluation part 13 data on the blank of the pressure gage 11 and data on a characteristic curve of the pressure gage 11. This characteristic curve is determined with known concentrations of live and/or active microorganisms of the same type as those expected to be present in the sample liquid 3, and data on the sample dilution can also be subsumed in the data on the characteristic curve of the pressure gage 11. The microprocessor 22 programmed in this way calculates a value of the concentration of live and/or active microorganisms in the sample from the data on the pressure provided by the pressure probe part 12 via the cable 14, and from the data which the microprocessor 22 receives from the data memories 23. Owing to this automated and programmed calculation it is possible to obtain a calculated value which represents directly as numerical value the concentration of live and/or active microorganisms in the sample and appears on a display 24 in the pressure evaluation part 13.

FIG. 10 illustrates a diagrammatically depicted ventilation implement, designated overall by 32, of an apparatus for carrying out the method according to the invention. Some parts of this ventilation implement 32 are identical to corresponding parts in the pressure probe part 12, and they may even be the same parts in a different function: such equivalent parts are only mentioned here, reference being made to the description given hereinbefore of their equivalents in connection with the pressure probe part 12.

The ventilation implement 32 includes a base 25 which is identical to the base 15. The test tube 1 fits in the same way into a bore 26, which is identical to the bore 16 and is likewise disposed with the axis vertical during use. An annular rim of the base 25 at the end of the bore 26 forms a stop face 27 which is identical to the stop face 17. The ventilation implement 32 additionally includes the previously mentioned hollow needle 7 and a cylindrical blind positioning socket 28, whose bore 29 is disposed with the axis vertical during use. The hollow needle 7 is firmly disposed on the positioning socket 28 parallel to the axis of the bore 29 but not coaxial thereto, i.e. eccentrically. An annular rim of the positioning socket 28 at the end of the bore 29 forms a stop face 30 in fixed position and coordination with the positioning socket 28 and consequently, via the hollow needle 7, with its tip 31. The axial length of the positioning socket 28 is such that, on use of the ventilation implement 32, the stopper 2 is pierced by the hollow needle 7 only to the extent, and the latter can be introduced into the interior of the test tube 1, only to the extent, that its tip 31 remains above the mixture 6 present in the test tube 1 in a headspace present therein. Finally, as is evident from FIG. 10, the ventilation implement 32, the test tube 1 and the stop faces 27 and 30 coordinated therewith have dimensions and are positioned relative to one another such that, when the stopper 2 is pierced by the hollow needle 7, only the latter comes into contact with the stopper 2, so that the latter is stressed only slightly and mainly only radially, and consequently is not pushed into the interior of the test tube 1, which would cause a volume change and measurement errors resulting therefrom, which are thus avoided.

FIG. 11 illustrates details of the stopper 2 depicted diagrammatically in axial longitudinal section. In order to ensure that the stopper 2 on the one hand is able to close the test tube 1 gas-tight, but on the other hand can be pierced by the hollow needles 7 and 9, this stopper 2 is produced from a chemical-resistant elastic plastic and is designed to be substantially mushroom-shaped, having a cylinder 33 which can be introduced into the test tube 1 and on which are shaped a head 34 at the top and a socket-like sealing lip 35 at the bottom. When the test tube 1 is closed with the stopper 2, the cylinder 34 and the sealing lip 35 are located, radially compressed, completely inside the test tube 1, whereas the somewhat wider head 33 remains outside the test tube 1 and covers its mouth. If, for example, the test tube 1 is a 15 ml Vacutainer® 16×125 mm tube from Becton Dickinson, and the stopper 2 consists of Viton® from Du Pont de Nemours, the total height of the stopper 2 to be pierced by the hollow needles 7 and 9 is about 5 mm, and the cylinder 34 is radially compressed by about 7%.

The invention has been described above by means of individual examples relating to the preparation of the substances of the invention and the bringing about and/or use of a modification of the kinetics of the enzymatic action of catalase. There are many possible uses of the substances of the invention, of the use thereof for modifying the kinetics of the enzymatic action of catalase and, where appropriate, for killing microorganisms, of the method according to the invention for measuring a concentration of live and/or active microorganisms, and of the corresponding apparatus according to the invention. Mention may be made, in a list of examples without any restriction thereto, as possible uses for measurement, for monitoring and/or for process control, and for killing microorganisms of: in the case of foodstuffs at the level of consumption, marketing and industry (against microbial spoilage); in the case of processing of materials by cutting (in relation to water-miscible cooling lubricants etc.); in the case of human medicine and veterinary medicine, in particular in supply and disposal in hospitals and medical laboratories (blood, urine, facilities and instruments, dressings etc.); in the supply of fresh water, in water storage and in sewage treatment; in ventilation and air-conditioning systems (fresh air purification, air circulation, waste air cleanup); and in research and development in the aforementioned or other areas.

In summary, it can be stated that with the catalase method according to the invention which has been depicted and described a) even very low microbe counts can be detected from a sample by filtration using suitable membrane filters;

b) a differentiation is possible between bacteria on the one hand, fungi and yeasts on the other hand, by filtration using suitable membrane filters; and c) a greater sensitivity of measurements is achieved because more sensitive pressure transducer probes than previously can be used;

and that the compound of the invention inactivates both active endogenous catalase and active bacterial catale, and can be used as active disinfection component alone or for further incorporation in disinfectants for killing microorganisms.

LIST OF REFERENCE NUMBERS 1 test tube
2 stopper
3 sample liquid
4 reagent liquid
5 hydrogen peroxide solution
6 mixture
7 hollow needle for pressure equalization
8 shaking back and forth
9 hollow needle for pressure measurement
10 pressure sensor
11 pressure gage
12 pressure probe part
13 pressure evaluation part
14 electric cable
15 base of the pressure probe part 12
16 bore in the base 15
17 stop face on the base 15
18 positioning socket
19 bore of the positioning socket 18

20 stop face on the positioning socket 18
21 tip of the hollow needle 9
22 microprocessor
23 data memory
24 display
25 base of the ventilation implement 32
26 bore in the base 25
27 stop face on the base 25
28 positioning socket
29 bore of the positioning socket 28
30 stop face on the positioning socket 18
31 tip of the hollow needle
32 ventilation implement
33 cylinder of the stopper 2
34 head of the stopper 2
35 sealing lip of the stopper 2

The invention claimed is:

1. A sulfonyl ester selected from the group consisting of:

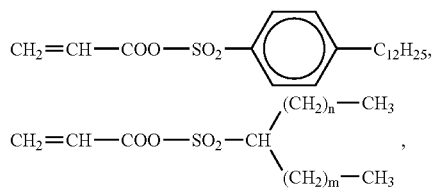

in which n and m are natural numbers and 3<(n+m)<60,

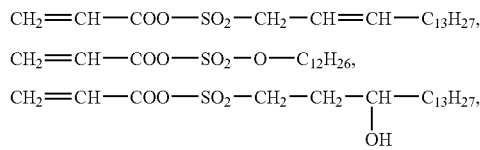

and
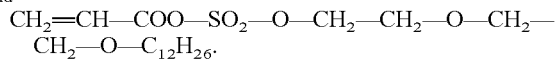
$CH_2=CH-COO-SO_2-O-CH_2-CH_2-O-CH_2-CH_2-O-C_{12}H_{26}$.

2. A method of modifying the kinetics of the enzymatic action of catalase by mixing said catalase with a compound as claimed in claim 1.

3. The method as claimed in claim 2, characterized in that the modification of the kinetics is an inactivation.

4. The method as claimed in claim 3, characterized in that the inactivation is irreversible.

5. The method as claimed in claim 4, characterized in that the inactivation relates to the enzymatic action of active endogenous catalase.

6. The method as claimed in claim 4, characterized in that the inactivation relates to the enzymatic action of active endogenous catalases.

7. The method as claimed in claim 6, characterized in that the inactivation relates to the enzymatic action of active endogenous catal ass without a noticeable inactivation of the enzymatic action of active intracellular catalase taking place.

8. The method as claimed in claim 4, characterized in that the inactivation relates to the enzymatic action of active endogenous catalase without a noticeable inactivation of the enzymatic action of active intracellular catalase taking place.

9. The method as claimed in claim 8, characterized in that the active intracellular catalase is that of live microorganisms.

10. The method as claimed in claim 7, characterized in that the active intracellular catalese is that of live microorganisms.

11. The method as claimed in claim 10, wherein the live microorganisms is selected from the group consisting of bacteria and fungi, Including molds and yeasts.

12. The method as claimed in claim 9, wherein the live microorganisms is selected from the group consisting of bacteria and fungi, including molds and yeasts.

13. The method as claimed in claim 12 for killing microorganisms.

14. The method as claimed in claim 11 for killing microorganisms.

15. The method as claimed in claim 10 for killing microorganisms.

16. The method as claimed in claim 9 for killing microorganisms.

17. The method as claimed in claim 8 for killing microorganisms.

18. The method as claimed in claim 7 for killing microorganisms.

19. The method as claimed in claim 6 for killing microorganisms.

20. The method as claimed in claim 5 for killing microorganisms.

21. The method as claimed in claim 4 for killing microorganisms.

22. The method as claimed in claim 3 for killing microorganisms.

23. The method as claimed in claim 2 for killing microorganisms.

* * * * *